US008753375B2

(12) United States Patent
Albertorio

(10) Patent No.: US 8,753,375 B2
(45) Date of Patent: *Jun. 17, 2014

(54) Z-SHAPED BUTTON FOR TISSUE REPAIR

(75) Inventor: Ricardo Albertorio, Naples, FL (US)

(73) Assignee: Arthrex, Inc., Naples, FL (US)

( * ) Notice: Subject to any disclaimer, the term of this patent is extended or adjusted under 35 U.S.C. 154(b) by 403 days.

This patent is subject to a terminal disclaimer.

(21) Appl. No.: 12/886,330

(22) Filed: Sep. 20, 2010

(65) Prior Publication Data

US 2011/0087280 A1  Apr. 14, 2011

Related U.S. Application Data

(60) Provisional application No. 61/251,593, filed on Oct. 14, 2009.

(51) Int. Cl.
*A61B 17/04* (2006.01)

(52) U.S. Cl.
USPC ............................................ 606/232; 606/60

(58) Field of Classification Search
USPC ................ 606/86 R, 60, 228, 232, 300, 308; 623/13.11–13.13; 128/898
See application file for complete search history.

(56) References Cited

U.S. PATENT DOCUMENTS

| | | | |
|---|---|---|---|
| 6,193,754 B1 * | 2/2001 | Seedhom | 623/13.11 |
| 2006/0020162 A1 | 1/2006 | Whayne et al. | |
| 2006/0190041 A1 | 8/2006 | Fallin et al. | |
| 2007/0049970 A1 | 3/2007 | Belef et al. | |
| 2007/0179531 A1 | 8/2007 | Thornes | |
| 2007/0185532 A1 | 8/2007 | Stone et al. | |
| 2008/0046009 A1 | 2/2008 | Albertorio et al. | |
| 2008/0082128 A1 * | 4/2008 | Stone | 606/232 |
| 2008/0177302 A1 | 7/2008 | Shurnas | |
| 2008/0208252 A1 | 8/2008 | Holmes | |

FOREIGN PATENT DOCUMENTS

EP  1 889 575 A2  2/2008

\* cited by examiner

*Primary Examiner* — Dianne Dornbusch
*Assistant Examiner* — Robert Lynch
(74) *Attorney, Agent, or Firm* — Dickstein Shapiro LLP

(57) ABSTRACT

Techniques and reconstruction systems for tissue repairs employing a Z-shaped button with a flexible strand or loop (which may have a fixed or adjustable length). The Z-shaped button has a distinctive Z-shape or an S-shape configuration, that allows a smaller length button to achieve comparable contact area as with a longer length button. The Z-shaped button allows for truncated flipping distance yet permits maximum cortical bone contact. The continuous loop/Z-shaped button construct may be used for fixation of bone to bone, or of soft tissue to bone.

14 Claims, 6 Drawing Sheets

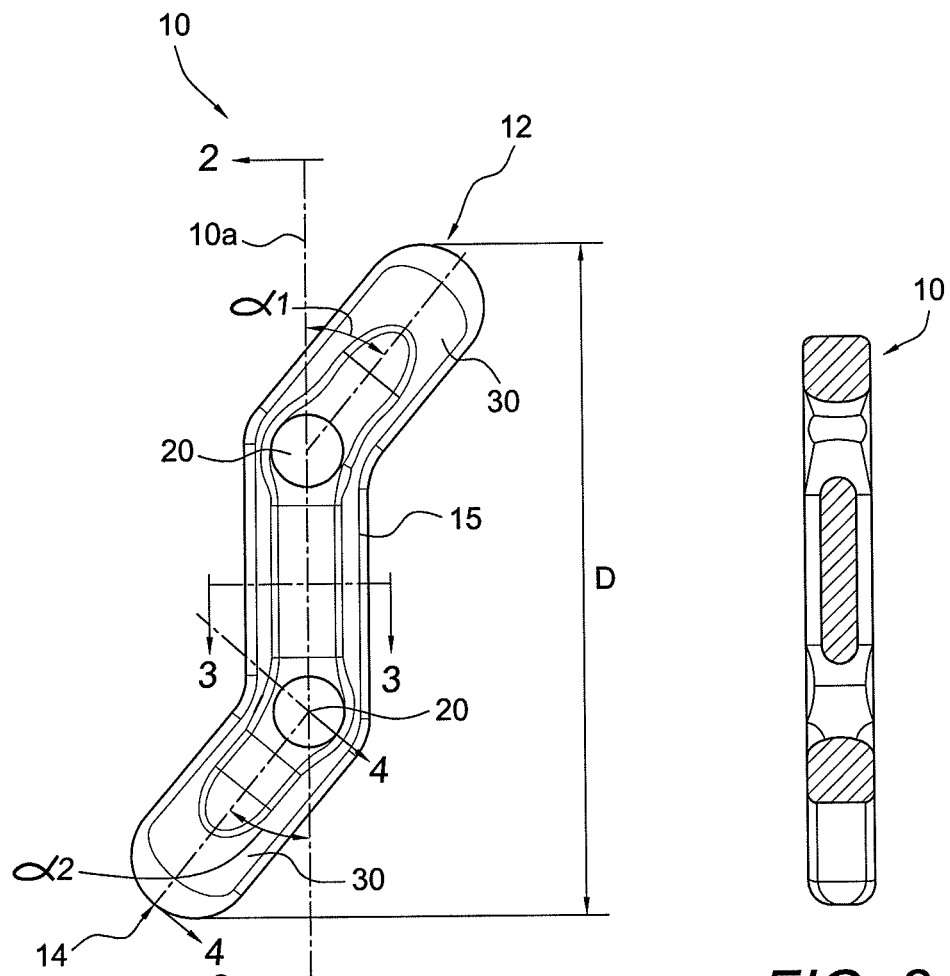
FIG. 1
FIG. 2
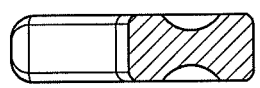
FIG. 3
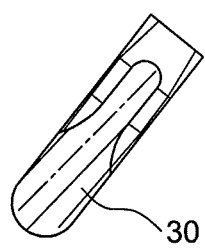
FIG. 4

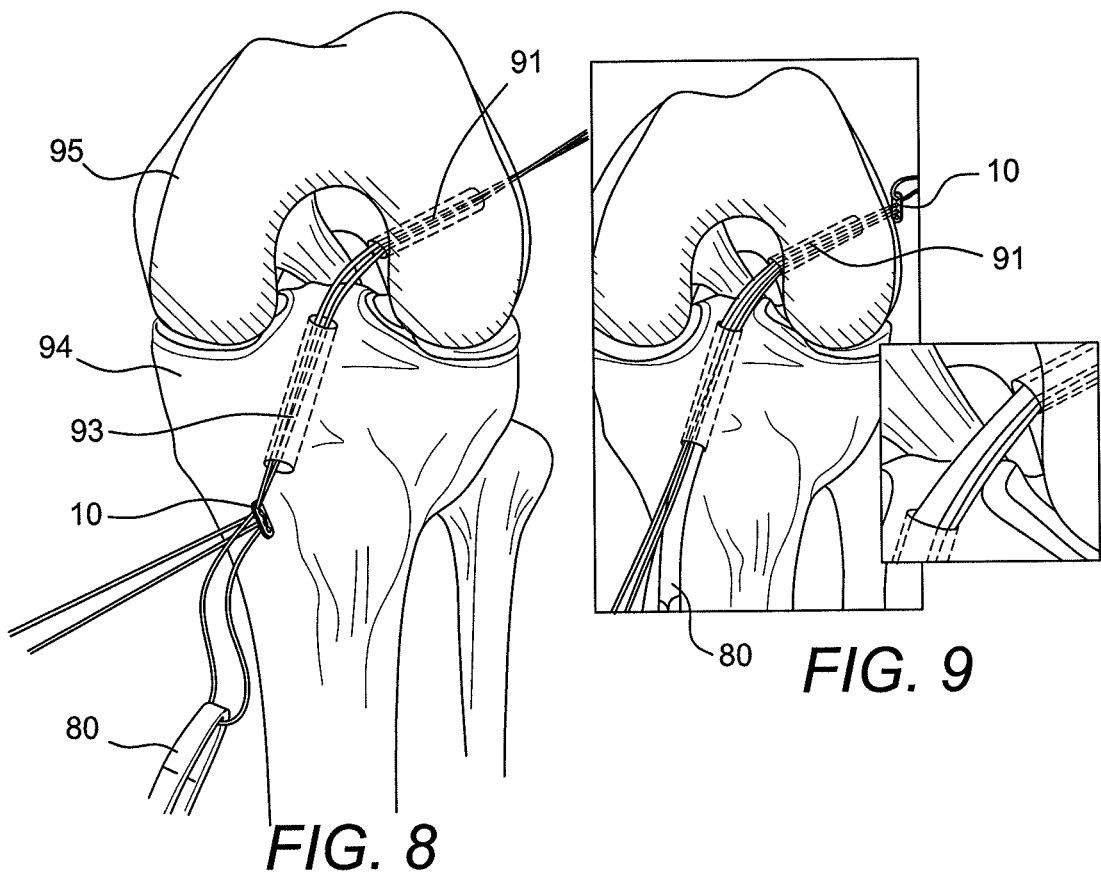
FIG. 8
FIG. 9
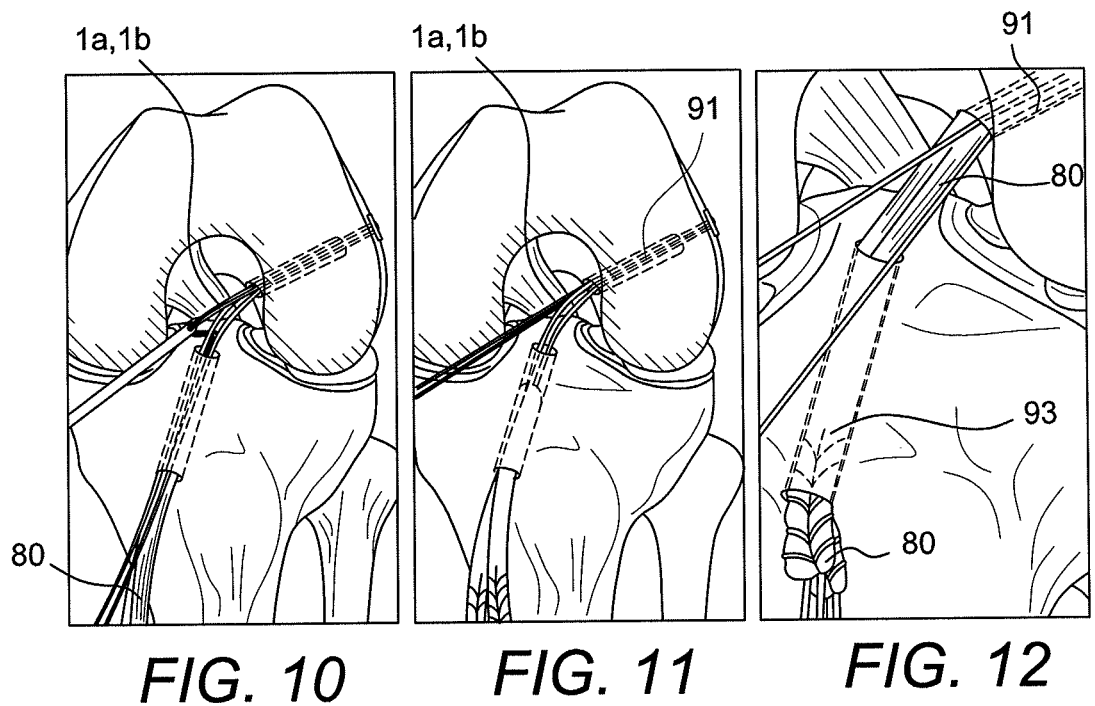
FIG. 10
FIG. 11
FIG. 12

Z-SHAPED BUTTON FOR TISSUE REPAIR

CROSS-REFERENCE TO RELATED APPLICATIONS

This application claims the benefit of U.S. Provisional Application No. 61/251,593, filed Oct. 14, 2009, the entire disclosure of which is incorporated by reference herein.

FIELD OF THE INVENTION

The present invention relates to surgical devices and, more particularly, to a novel button construct.

BACKGROUND OF THE INVENTION

Suture-button constructs have been used for fixation of ligaments in anterior cruciate ligament (ACL) reconstruction as shown, for example, in U.S. Patent Application Publication No. 2008/0046009, incorporated herein by reference. The suture-button construct disclosed in this patent application is formed of a button and a continuous suture loop passing through the button. The surgical method of ACL reconstruction includes the step of looping a graft (such as a semitendinosus allograft) over the continuous loop attached to a button and then fixing the graft in a femoral socket by inter alia (i) passing the button with the continuous loop and graft lengthwise through a tunnel in the femur, and (ii) flipping the button once it exits the femoral cortex to secure the button to the femur, thereby securing the attached graft within the femoral socket.

When an oblong button is employed to pull the graft through the tunnel in ACL reconstruction, the oblong button, when flipped, provides increased cortical bone contact which, in turn, allows increased graft fixation. However, a longer oblong button requires a longer suture (or suture loop) to flip the button on the femoral cortex. That is, a longer, oblong button requires a longer suture to pull the full length of the oblong button out of the tunnel, so that the button has enough room to flip on the cortex. For example, a 20 mm long straight button needs to exit the lateral cortex for at least about 20 mm, to allow for enough flipping distance.

A novel button construct that requires decreased flipping distance while providing maximum cortical bone contact and maximum graft fixation is desired.

SUMMARY OF THE INVENTION

The present invention provides a device and method of ligament reconstruction. The device of the present invention allows for suspensory-type fixation of grafts within full-diameter bone tunnels or sockets.

The present invention provides a button having a distinctive Z-shape or an S-shape configuration, that allows a smaller length button to achieve comparable contact area as with a longer length button. The Z-shaped button (Z-button) of the present invention allows for truncated flipping distance yet permits maximum cortical bone contact. For example, while a 20 mm straight button needs to exit the lateral cortex for about 20 mm (i.e., requires a flipping distance of about 20 mm), the Z-button of the present invention requires only about 18.5 mm (i.e., requires a flipping distance of about 18.5 mm) but would span about 22 mm, providing improved bone contact and graft fixation.

The present invention also provides techniques for fixation of soft tissue to bone, or of bone to bone, with a Z-shaped or S-shaped button.

These and other features and advantages of the invention will be more apparent from the following detailed description that is provided in connection with the accompanying drawing and illustrated exemplary embodiments of the invention.

BRIEF DESCRIPTION OF THE DRAWING

FIG. 1 illustrates a top planar view of a Z-button according to an exemplary embodiment of the present invention.

FIG. 2 illustrates a cross-sectional view of the Z-button of FIG. 1, taken along line C-C.

FIG. 3 illustrates a cross-sectional view of the Z-button of FIG. 1, taken along line D-D.

FIG. 4 illustrates a cross-sectional view of the Z-button of FIG. 1, taken along line F-F.

FIGS. 8-18 illustrate subsequent steps of an exemplary method of tissue reconstruction according to the present invention and employing the assembly of FIG. 7.

DETAILED DESCRIPTION OF THE PREFERRED EMBODIMENTS

The present invention provides a device and method of ligament reconstruction. The device of the present invention allows for suspensory-type fixation of grafts within full-diameter bone tunnels or sockets.

The present invention provides a button having a distinctive Z-shape or an S-shape configuration, that allows a smaller length button to achieve comparable contact area as with a longer length button. The Z-shaped button of the present invention allows for truncated flipping distance yet permits maximum cortical bone contact. For example, while a 20 mm straight button needs to exit the lateral cortex for about 20 mm (i.e., requires a flipping distance of about 20 mm), the Z-button of the present invention requires only about 18.5 mm (i.e., requires a flipping distance of about 18.5 mm) but would span about 22 mm, providing improved bone contact and graft fixation.

The present invention also provides techniques for fixation of soft tissue to bone, or of bone to bone, with a Z-shaped or S-shaped button. In exemplary embodiments only and as detailed below, the Z-shaped or S-shaped button of the present invention is used to secure a soft tissue graft in a bone socket in a retrograde manner, for example, or to secure a bone-to-bone (BTB) graft in a femoral tunnel or socket in a retrograde manner, for example. The bone socket or tunnel may be formed by a conventional (antegrade manner) or by a retrograde manner (for example, by employing a retrodrill cutter). The Z-shaped or S-shaped button may be employed with a fixed loop or an adjustable loop (for example, with an adjustable loop length that allows adjustment in one direction while preventing or locking the construct from loosening in the opposite direction, due to applied tensile forces).

Figure 5:
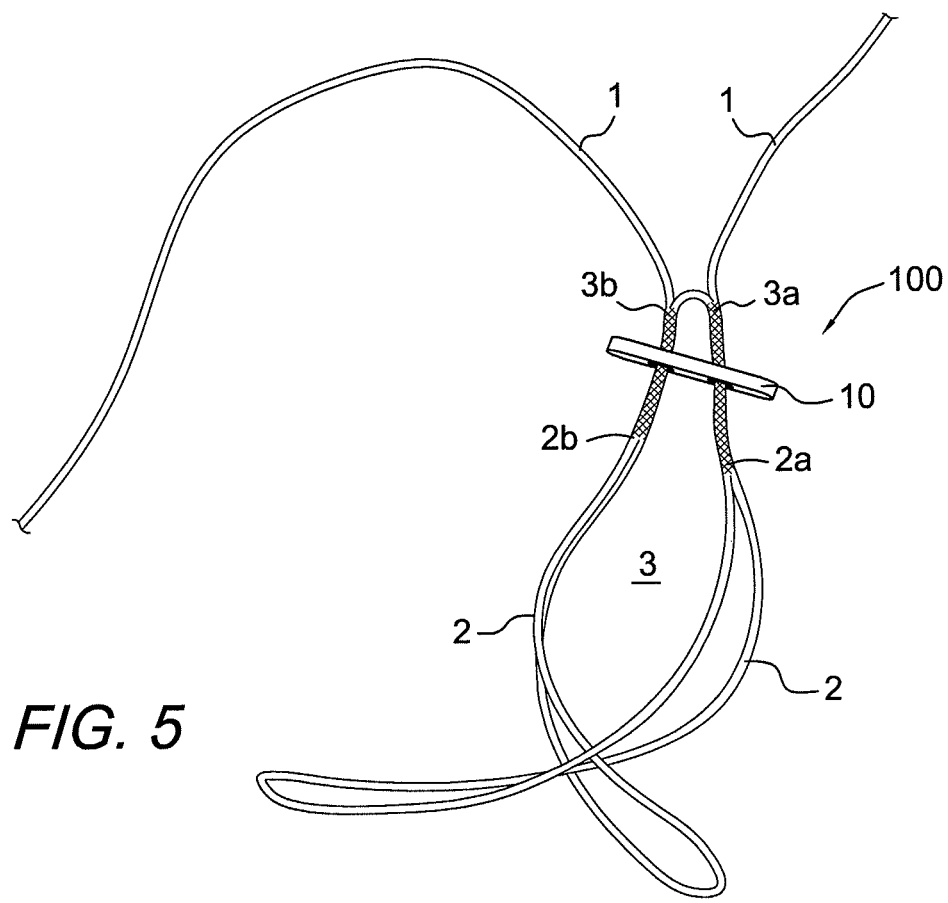
FIGS. 5 and 6 illustrate an exemplary button/loop construct of the present invention with the Z-button of FIG. 1 and a flexible, adjustable loop (showing the splicing marked with different colors for easy identification).
Figure 6:
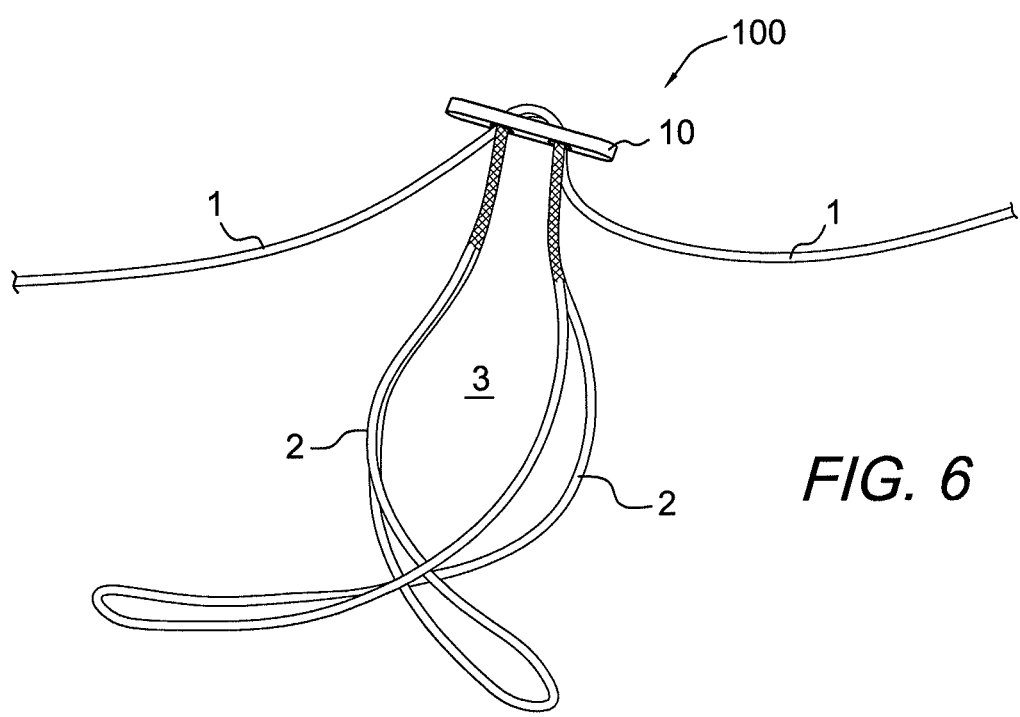
Figure 7:
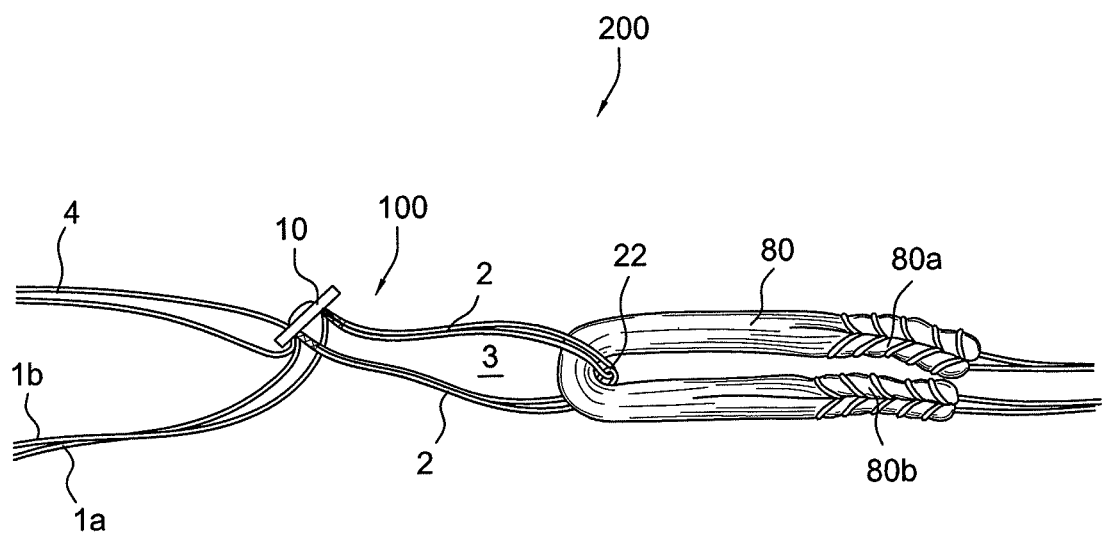
FIG. 7 illustrates the assembly of FIG. 5 and further provided with tissue (a graft or ligament, for example) looped over the eyesplice interconnection of the adjustable loop.

Referring now to the drawings, where like elements are designated by like reference numerals, FIGS. 1-4 illustrate a Z-button 10 of the present invention having a shape that allows for a smaller length button to achieve comparable contact area as with a longer length button. FIGS. 5-7 illustrate the Z-button 10 of FIGS. 1-4 employed in the formation of an exemplary adjustable suture button construct 100 for securing tissue (for example, soft tissue, graft, tendon, ligament, synthetic material, bone, or combinations of such materials, among others) to bone. The tissue may be directly looped over the flexible, adjustable loop for insertion into a bone tunnel or socket. Alternatively, the tissue may be looped over a tissue supporting device (such as a wedge, for example) that is connected to the flexible, adjustable loop for further insertion into a bone tunnel or socket. FIGS. 8-18 illustrate the insertion and fixation of adjustable suture button construct 100 (with the Z-button 10 of the present invention) within femoral and tibial tunnels.

The Z-shaped button 10 of the present invention allows for truncated flipping distance yet permits maximum cortical bone contact. For example, while a 20 mm straight or oblong button needs to exit the lateral cortex for about 20 mm (the flipping distance), the Z-button 10 needs only about 18.5 mm for the flipping distance D (FIG. 1), but would span about 22 mm (i.e., the distance D1 between most distal end 12 to most proximal end 14).

Z-button 10 of the present invention is provided with two openings or inside-eyelets 20 that allow the passage of a flexible material (for example, a suture strand or a suture loop). Preferably, the two openings or eyelets 20 are provided on a longitudinal axis 10a of body 15 of the button 10. Two sides, arms or extensions 30 extend from the body 10 as shown in FIG. 1 (i.e., diametrically opposed relative to axis 10a). One of the two sides or arms 30 forms an angle α1 of about 45 degrees with the axis 10a, while the other of the two sides or arms 30 forms another angle α2 with the axis 10a. Preferably, angle α1 is about equal to angle α2 (i.e., both of about 45 degrees, as shown in FIG. 1) but may be also different.

Sides or extensions 30 may be preferably formed of a material similar to that of the body 15. The button 10 may be formed, for example, of homogeneous or heterogeneous biomaterials, with or without additives such as ceramics. In exemplary embodiments only, button 10 (including sides 30 and body 15) may be formed of a metal such as titanium or titanium alloy, PEEK or PLLA. The flexible material may be suture such as FiberWire® suture, sold by Arthrex, Inc. of Naples, Fla.

Z-button 10 of the present invention may be used with a continuous fixed diameter loop, or with an adjustable loop, or with a combination of fixed and adjustable loops (and further in combination with other flexible strands, as desired, and as detailed below). For example, the Z-button 10 may be employed with a continuous loop to form a continuous loop/Z-button construct used for fixation of bone to bone, or of soft tissue to bone. The openings or inside eyelets 20 allow the passage of a continuous loop, preferably a suture loop. The suture may be a single high strength suture such as FiberWire® suture, or may be formed of a plurality of suture strands configured to separate from a single strand to a plurality of strands in the continuous loop. The continuous loop/Z-button construct of the present invention may be used for fixation of bone to bone, or of soft tissue to bone. An exemplary system and method of fixation of ligaments which may employ the Z-button 10 is detailed for example in U.S. Patent Publication No. 2008/0046009 (the disclosure of which is incorporated in its entirety herewith), wherein the oblong button described in U.S. Patent Publication No. 2008/0046009 is substituted with the Z-button 10 of the present invention.

Z-button 10 of the present invention may be also used with an adjustable loop, for example, with a self-locking adjustable loop as detailed in U.S. application Ser. No. 12/751,897 (filed on Mar. 31, 2010) and U.S. application Ser. No. 12/751,835 (filed on Mar. 31, 2010), the disclosures of both of which are also incorporated by reference in their entirety herewith.

FIG. 5 illustrates an exemplary self-locking adjustable construct 100 comprising Z-shaped button 10 and flexible material 1 with two adjustable eyesplices (2) that are interconnected to form one adjustable loop (3), as detailed in U.S. application Ser. Nos. 12/751,897 and 12/751,835. By pulling on the free braid strands (1), the individual eyesplices (2) constrict and, in turn, reduce the loop length of loop (3). In order for loop (3) to elongate, a force needs to be applied interior to one or both of the eyesplices (2) to elongate the individual loops.

FIG. 5 illustrates free strands 1 of the self-locking adjustable construct 100 pulled back through the Z-shaped button 10 to expose the splice exits points 3a, 3b. Also shown in FIG. 5 are two splice entrance points 2a, 2b. FIG. 6 shows the Z-shaped button 10 adjusted downward to give full view of the two splice entrance points 2a, 2b and the two splice exit points 3a, 3b. FIG. 6 illustrates the final self-locking adjustable construct 100 with no additional splicing occurring and with the free strands 1 passed through the opposite button holes of the Z-shaped button 10.

Details for forming/assembling construct 100 of FIGS. 5 and 6 are detailed in both U.S. application Ser. Nos. 12/751,897 and 12/751,835, and include as starting materials a suture strand (for example, 50 inches of braided UHMWPE strand); a needle (for example, a blunt tip needle with nitinol loop) and a button (for example, a titanium Z-button). The suture strand is folded to create two equal length parallel braid strands. At this step, the braid is folded at the midpoint, 25 inches, to create two parallel equal length braid strands (Step 1). At Step 2, a first eyesplice is created on the first strand of braid by passing the blunt tip needle through the center of the braid with the end of the braid being carried through in the nitinol loop of the needle. The splice should travel for a distance of about 17-19 mm through the braid towards the braid midpoint created in Step 1.

Once the first eyesplice has been formed, at Step 3, the Z-button is slid over the non-spliced strand passing the strand through both button holes. The Z-button is slid so that it rests over the first spliced section. At Step 4, a second eyesplice is formed, similar to the first one, with the opposing strand. The strand should be looped through the first eyesplice loop resulting in two eyesplice loops that are interconnected. Again, the splice length should be between 17-19 mm. The splice should be created such that the exiting aperture of the splice is as close as possible to the first eyesplice.

The self-locking adjustable construct 100 may be used with additional fixation devices, for example, with at least a wedge, an implant, a plug, or an anchor for supporting a graft or a ligament, for improved fixation and exact determination of the graft length within the bone sockets (as detailed in U.S. application Ser. Nos. 12/751,897 and 12/751,835).

FIG. 7 illustrates tissue 80 (with stitched ends 80a, 80b) looped directly over eyesplice interconnection 22 of the adjustable loop 3 of the button/loop construct 100 of the invention to form reconstruction assembly 200 (employed in method of ACL reconstruction according to an exemplary embodiment of the invention). Loop shortening strands 1a, 1b of the flexible strand 1 are used to control and adjust the length of the loop 3.

FIGS. 8-18 illustrate subsequent steps of an exemplary method of securing reconstruction assembly 200 of FIG. 7 (with the button/loop construct 100 and looped graft 80) to bone.

The femoral socket 91 may be drilled transtibially, or through the medial portal, or by a retrograde technique. The femoral socket 91 is drilled in femur 95 to a depth about equal to the amount of graft desired in the femoral socket. After creating the tibial tunnel 93, a passing suture 4 (FIG. 7) is brought through tibia 94 and out the femur (FIGS. 8 and 9). The Z-button 10 is positioned so that the nonlooped side is facing lateral. The Z-button 10 is pulled through the femur until it exits the lateral cortex to achieve fixation (FIG. 9). No tension should be put on the loop shortening strands until the button has been passed, self-flips, and is fully seated against the cortex, as this could compromise graft advancement.

Referring now to FIGS. 10-12, the marked loop shortening strands 1a, 1b are retrieved from the implant through the medial portal. The graft is advanced and tension is pulled on the loop shortening strands. The graft will be completely seated when the mark on the graft reaches the femoral socket (FIG. 12).

Figures 13, 14, 15:
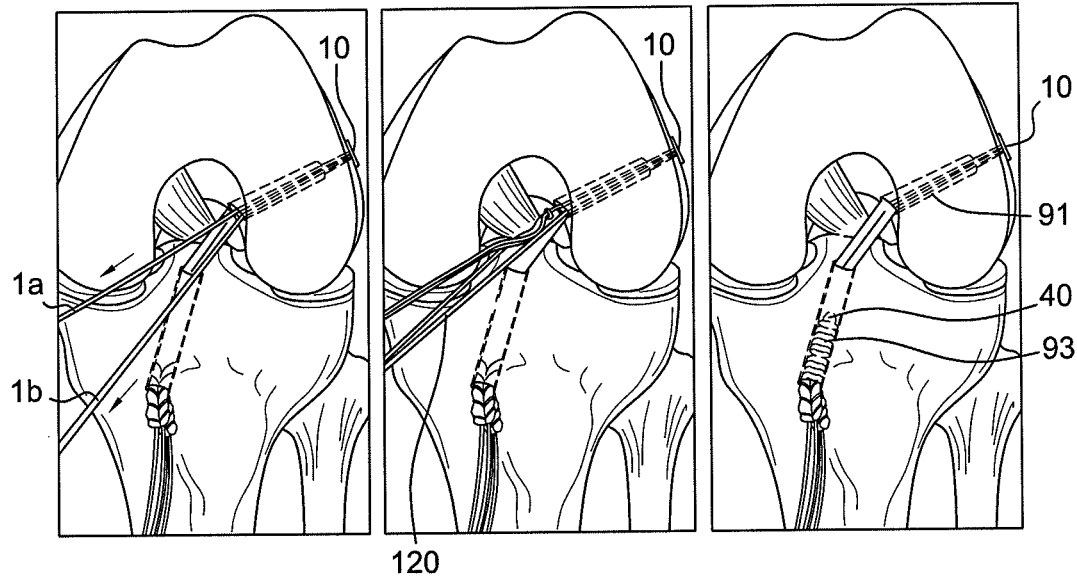

The graft shortening strands 1a, 1b are pulled individually for final graft tensioning (FIGS. 13-15). The graft shortening strands are cut with a cutting instrument 120 (FIG. 14) such as an arthroscopic #2 FiberWire® cutter. The technique proceeds with tibial fixation with fixation device 20a.

Figure 16:
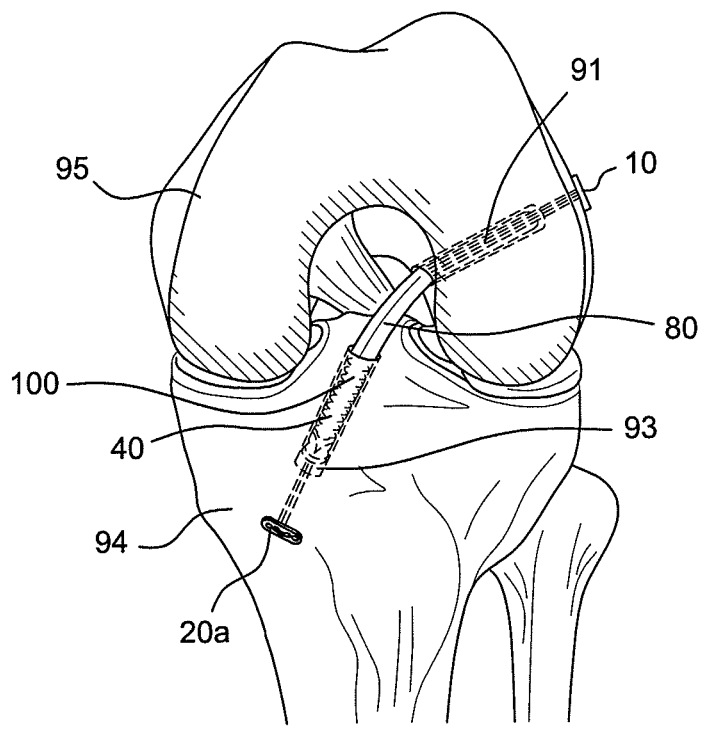

The button/loop construct 100 is also ideal for all-inside ACL reconstruction (FIG. 16). The adjustability of the implant simplifies graft length determination and allows graft tensioning from the femoral side.

Figure 17:
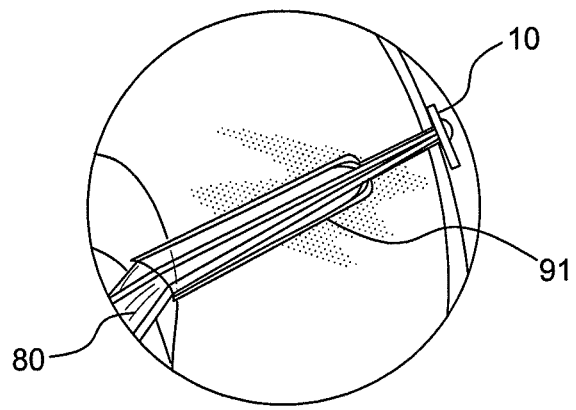
Figure 18:
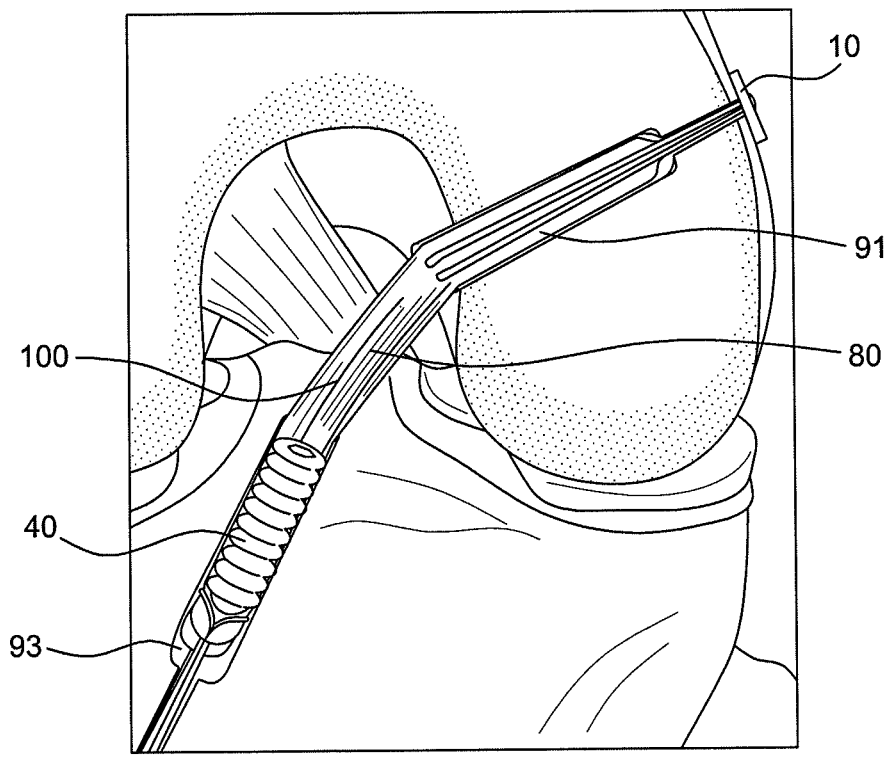

FIG. 17 illustrates a detailed view of the femoral graft of FIG. 16. FIG. 19 illustrates an enlarged view of the final construct of FIG. 16 with tissue (graft) 80 secured within femoral socket 91 and tibia socket 93 by adjustable button/loop construct 100 and an interference device 40.

The adjustable loop of the self-locking adjustable knotless construct 100 is adjustable under tension when the surgeon simply pulls on both ends of the final construct 100 to adjust the length of the flexible loop and to tighten, therefore, the construct. The Z-button 10 is pulled out of the bone cortex with the passing sutures (which are later discarded) and self-flips onto the cortex immediately upon exiting.

The ACL reconstruction detailed above offers adjustable cortical fixation for cruciate ligament reconstruction. The four-point knotless fixation of the self-locking adjustable knotless construct 100 resists cyclic displacement and offers maximum loads equal to closed loop devices. The present invention eliminates the need for multiple sized loops and facilitates complete graft fill of short femoral sockets that are common with anatomic ACL drilling. The Z-button requires decreased flipping distance while providing maximum cortical bone contact and maximum graft fixation. The Z-button also allows for suspensory-type fixation of grafts (such as tissue 80) within full-diameter bone tunnels or sockets.

Although the embodiments above have been described with reference to particular ACL reconstruction techniques, the invention is not limited to these exemplary embodiments. Accordingly, the present invention also contemplates embodiments wherein a flexible loop attached to Z-button 10 of the present invention is employed for additional tissue positioning and/or tissue adjustment applications, for example, in fixation of bone to bone (such as small joint applications, or acromioclavicular joint fixation techniques) which employ two fixation devices (for example, two buttons) joined by a continuous suture loop. In these applications, a second button (for example, another Z-button) is used in conjunction with the Z-button 10 and with flexible material between the two buttons.

In exemplary embodiments only, the self-locking adjustable knotless construct 100 of the present invention may be employed in a method of bunion repair as described in U.S. Patent Publ. No. 2008/0208252, and/or in a method of Lisfranc repair as described in U.S. Patent Publ. No. 2008/0177302, the disclosures of both of which are incorporated by reference in their entirety herewith (wherein the adjustable suture loop of self-locking adjustable knotless construct 100 would be provided with an additional second button). Similarly, the self-locking adjustable knotless construct 100 of the present invention may be employed in a method of fixation of bone to bone as described in U.S. Patent Publ. No. 2007/0179531, the disclosure of which is incorporated by reference in its entirety herewith (wherein the adjustable suture loop of self-locking adjustable knotless construct 100 would be provided with an additional second button, so that the adjustable loop extends between a plurality of bone tunnels and secures at least a first bone to a second bone).

In the above-noted exemplary embodiments, the self-locking adjustable knotless construct 100 is not provided with a graft supporting deice (wedge) (as in U.S. application Ser. Nos. 12/751,897 and 12/751,835) and, instead of a wedge/plug or screw, a second button can be used (the second button may be round, oblong, and with any number of apertures, or may be another Z-button). The buttons may have a similar or different configuration and they may have at least one hole or aperture (such as Z-button 10 with two apertures, or a button with only one aperture). The two buttons/adjustable loop system of the present invention (comprising two buttons with a continuous loop of flexible material having an adjustable length and perimeter, at least one of the buttons being a Z-button) may thus be used for syndesmosis, Lisfranc, and bunion repair, among others, with an adjustable loop construct.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of positioning tissue within the body, comprising the steps of:
   providing a suture loop/button construct having a Z-shaped button with at least one eyelet and a continuous suture loop attached to the at least one eyelet, wherein the Z-shaped button comprises a body with a longitudinal axis and two opposing parallel arms extending from opposite ends of the body, each arm disposed at an angle of 45 degrees with respect to the longitudinal axis;
   providing the suture loop/button construct in the vicinity of tissue to be positioned;
   attaching the tissue to be positioned to the suture loop/button construct;
   inserting the suture loop/button construct and the attached tissue within a socket or a tunnel in a bone;
   pulling the suture loop/button construct with the attached tissue through the socket or the tunnel in the bone until the Z-shaped button exits the socket or the tunnel in the bone and is outside the bone; and
   flipping and securing the Z-shaped button on a surface of the bone, wherein the Z-shaped configuration of the button provides increased contact with the surface of the bone as compared to a straight oblong button.

2. The method of claim 1, wherein the step of attaching the tissue further comprises folding the tissue over the continuous suture loop.

3. The method of claim 1, wherein the tissue to be positioned is biological or non-biological tissue.

4. The method of claim 1, wherein the tissue to be positioned is selected from the group consisting of ligament, tendon, bone and cartilage.

5. The method of claim 1, wherein the tissue to be positioned is soft tissue graft or BTB graft.

6. A method of conducting arthroscopic surgery, comprising the steps of:
forming a bone tunnel or socket;
providing a suture loop/button construct in the vicinity of the bone tunnel or socket, the suture loop/button construct comprising a Z-shaped button having at least one eyelet, and a continuous suture loop attached to the at least one eyelet, wherein the Z-shaped button comprises a body with a longitudinal axis and two opposing parallel arms extending from opposite ends of the body, each arm disposed at an angle of 45 degrees with respect to the longitudinal axis;
attaching a graft to the suture loop/button construct;
inserting the graft attached to the suture loop/button construct within the bone tunnel or socket and passing the suture loop/button construct through the bone tunnel or socket until the Z-shaped button exits the bone tunnel or socket and is outside the bone; and
subsequently securing the graft within the bone tunnel or socket by flipping and securing the Z-shaped button to a bone cortex abutting the bone tunnel or socket, wherein the Z-shaped configuration of the button provides increased contact with the bone cortex as compared to a straight oblong button.

7. The method of claim 6, wherein the graft is soft tissue graft or BTB graft.

8. The method of claim 6, wherein the bone tunnel or socket is a femoral or tibial bone tunnel or socket.

9. The method of claim 6, wherein the Z-shaped button has a length of about 18.5 mm.

10. A method of tissue reconstruction, comprising:
providing a construct comprising an adjustable button/loop construct having a Z-shaped button and a flexible, adjustable loop connected to the button, the flexible loop having an adjustable length, wherein the Z-shaped button comprises a body with a longitudinal axis and two opposing parallel arms extending from opposite ends of the body, each arm disposed at an angle of 45 degrees with respect to the longitudinal axis; and a tissue connected to the flexible, adjustable loop;
inserting the construct within a first bone tunnel and a second bone tunnel;
advancing the construct through the first bone tunnel until the Z-shaped button exits the first bone, and then pivots and engages a cortical surface of the first bone, wherein the Z-shaped configuration of the button provides increased contact with the cortical surface of the first bone as compared to a straight oblong button; and
adjusting the length of the loop to secure the tissue within the first and second bone tunnels.

11. The method of claim 10, further comprising the steps of:
attaching the loop to the Z-shaped button by forming an eyesplice interconnection on the loop and positioning the Z-shaped button over the eyesplice interconnection;
passing the tissue through the loop and looping the tissue over the loop to form a double looped tissue; and
adjusting the length of the loop to position the double looped tissue within the first bone tunnel.

12. The method of claim 10, wherein the tissue is soft tissue, graft, tendon, ligament, synthetic material, biological material, bone, or a combination of such materials.

13. The method of claim 10, wherein the construct is formed by the steps of:
providing a suture strand having two ends;
attaching one end to a suture passing device;
passing the suture passing device through the center of the suture strand to form a first eyesplice with one of the two ends;
sliding the Z-shaped button over a non-spliced strand so that the Z-shaped button rests over the spliced strand; and
passing the suture passing device through the center of the first eyesplice to form a second eyesplice with the other of the two ends, wherein the first eyesplice is interconnected to the second eyesplice.

14. The method of claim 13, wherein the suture passing device is a needle.

* * * * *